CHRYSANTHEMUM PLANT

Filed Jan. 8, 1971 2 Sheets-Sheet 1

INVENTORS
WALTER H. JESSEL, JR.,
WILLIAM E. DUFFETT
BY
Oberlin, Maky, Donnelly & Renner
ATTORNEYS INVENTORS
WALTER H. JESSEL, JR.,
WILLIAM E. DUFFETT
BY
Oberlin, Maky, Donnelly & Renner
ATTORNEYS

United States Patent Office

Plant Pat. 3,255

Patented Aug. 15, 1972

3,255

CHRYSANTHEMUM PLANT

Walter H. Jessel, Jr., Doylestown, and William E. Duffett, Akron, Ohio, assignors to Yoder Brothers, Inc., Barberton, Ohio

Filed Jan. 8, 1971, Ser. No. 105,138

Int. Cl. A01h *5/00*

U.S. Cl. Plt.—80 1 Claim

Figure 1:
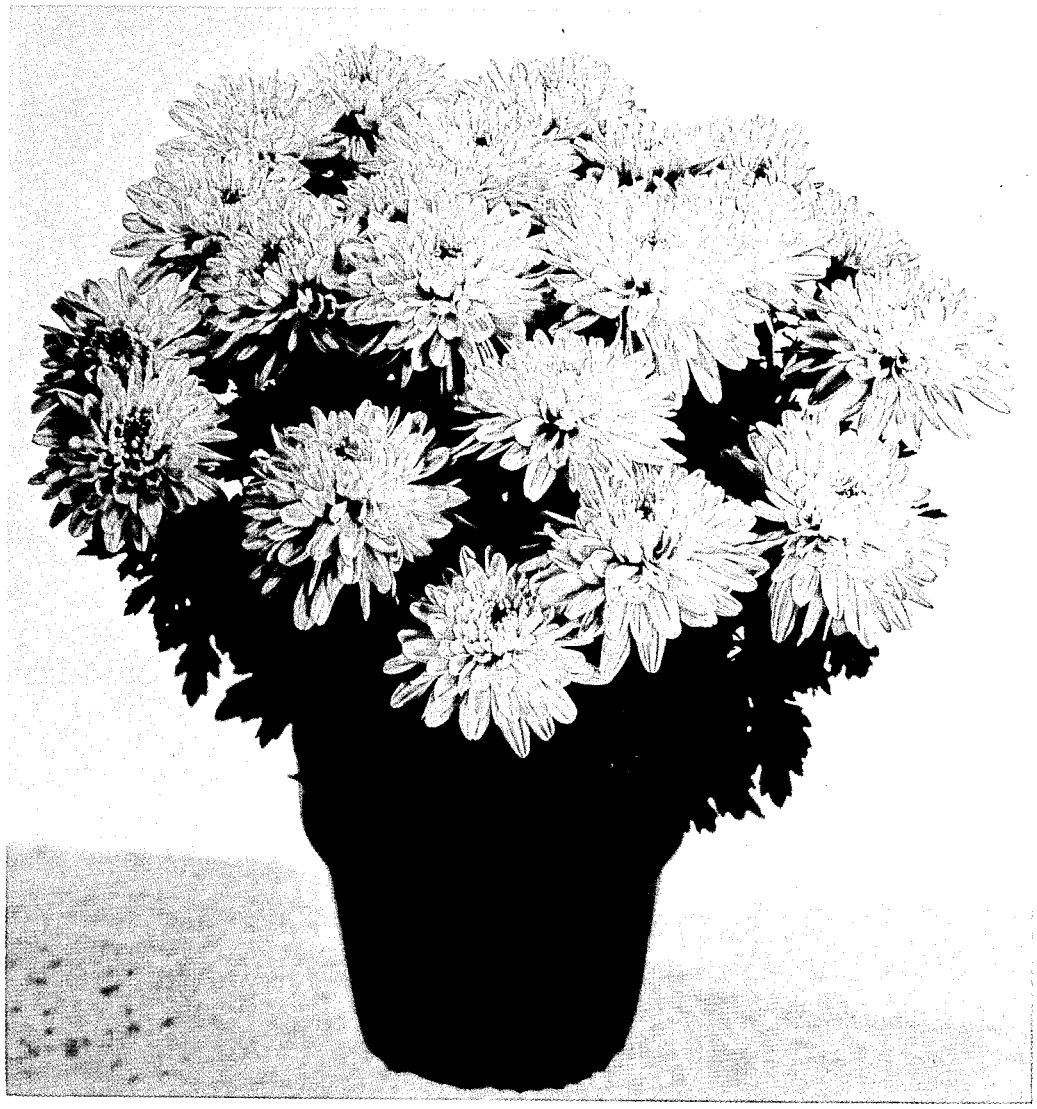
Figure 2:
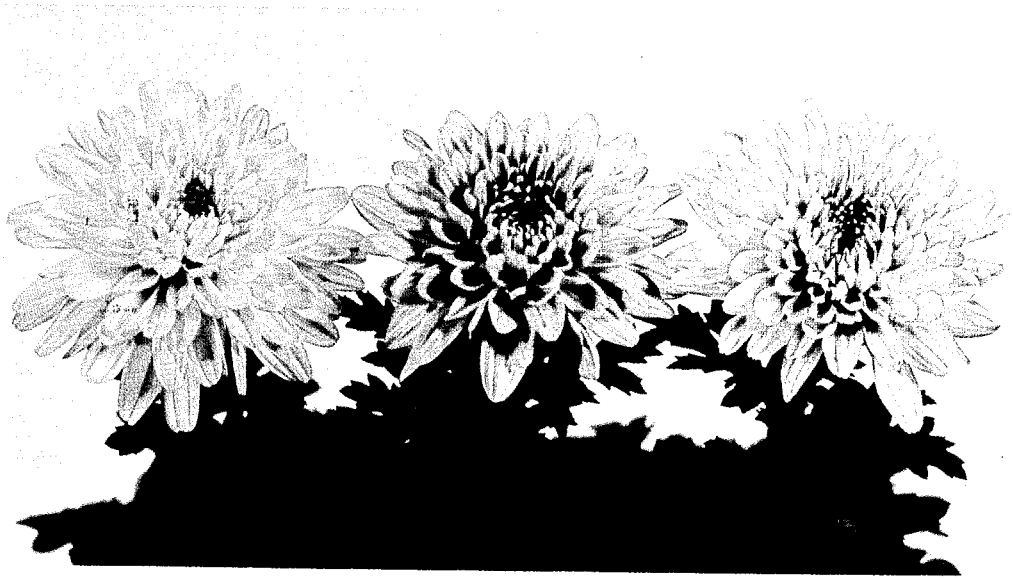

The present invention comprises a new and distinct cultivar of chrysanthemum plant which is a sport of the unpatented but well-known commercial cultivar known in the United States as Snowpink.

The new cultivar is similar in many respects to the parent cultivar Snowpink, having the same characteristics of:

(1) Foliage shape.
(2) Foliage color.
(3) Flower form.

The new cultivar is distinguished from Snowpink by the following characteristics:

(1) 2"–3" more vigor, which enables a grower to produce it with one less long day week.
(2) 5–7 days later flowering response.
(3) ½" larger flower, producing a showier pot.
(4) Longer flower form retention, which contributes to a longer bench life.
(5) Less lavender tones in flowers, thereby producing a truer pink tonality. Under incandescent lights particularly the new cultivar is brighter and the color resembles a glowing carnation pink.

The new cultivar was selected from a flowering block of the parent cultivar in Barberton, Ohio, and when asexually reproduced by cuttings at Barberton, Ohio, the new cultivar has been found to retain its distinctive characteristics through successive propagations.

The new cultivar when grown in the vicinity of Barberton, Ohio, has a response period of approximately nine weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the northern and western United States and coastal California is from January through December, Florida, December through April.

In the accompanying drawings sheet 1 comprises a photograph of the new cultivar by itself, and sheet 2 comprises a color comparison photograph, with the new cultivar appearing on the left and the cultivars Always Pink and Deep Snow Pink, also sports of Snowpink, appearing in the middle and on the right of the photograph, respectively. Both Always Pink and Deep Snow Pink are commercially available cultivars of Yoder Brothers, Inc., Barberton, Ohio, with Always Pink forming the subject matter of application Ser. No. 111,159, filed Jan. 29, 1971. The pink tonality of the new cultivar is especially evident in the comparison photograph.

In the following descriptions, color references are to the Munsell Color Book, 1963 edition, and comparisons are made with the cultivar Snowpink. Where only one value or description appears for the new cultivar, such value or description applies also to the comparison cultivar.

BOTANICAL CLASSIFICATION: *Chrysanthemum morifolium*

| Bloom | Glo Pink | Snowpink |
|---|---|---|
| Bloom: | | |
| Size | 3½" | 3". |
| Fully expanded | 4" | 3½". |
| Borne | Singly on disbudded shoots or clusters on nondisbudded shoots. | |
| Stems | Strong. | |
| Form | Decorative. | |
| Permanence | 14 days. | |
| Color: | | |
| Center of flower | Dark lavender, 2.5RP5/6; Lavender, 2.5RP6/6 | Lavender, 2.5RP7/6. |
| Base of petals | Lavender pink, 10P7/8; Light lavender pink, 10P8/6 | Lavender, 2.5RP7/6; Light lavender, 10P8/4. |
| Inside of petals | do | Do. |
| Reverse of petals | Lavender, 10P7/4; Light lavender, 10P8/4 | Light lavender, 10P8/4; Pale lavender, 10P9/2. |
| Tonality from a distance | Lavender pink | Lavender. |
| Discoloration | Light lavender pink | Light lavender. |
| Petals: | | |
| Texture | Smooth. | |
| Appearance and form | Open at base, broaden quickly, shallow ridged keel tapering to a blunt point. | |
| Arrangement | Composite, whorled on a single receptacle. | |
| Persistence | Resist shatter. | |
| Fragrance | Typical chrysanthemum. | |
| Reproductive organ: | | |
| Stamen, anthers | None to five. | |
| Pollen | None to very scant. | |
| Arrangement | Clustered in center of flowers, if present. | |
| Styles | Present both ray and disc florets. | |
| Length | Short. | |
| Ovaries | At the base of petal attached to receptacle. | |
| Plant: | | |
| Form | Herbaceous. | |
| Growth | Semi-upright. | |
| Height | 13" | 10½". |
| Spread | Moderate. | |
| Foliage: | | |
| Top side | Green, 10GY4/4. | |
| Size | 4½" long, 2¾" wide | 4" long, 2½" wide. |
| Quantity | Numerous. | |
| Shape | Spatulate lobed. | |
| Texture | Smooth. | |
| Ribs and veins | Moderate prominent. | |
| Edge | Moderate indented. | |
| Serration | Slight. | |
| Under side | Light green 7.5GY6/4. | |
| Stipules | Small. | |

We claim:

1. A new and distinct cultivar of chrysanthemum characterized particularly as to its uniqueness when compared to the parent cultivar Snowpink by its 2–3″ more vigor, 5–7 days later flowering response, ½″ larger flower, longer form retention, less lavender tones in flower thereby producing a truer pink tonality, and foliage which is approximately one half inch longer and one quarter inch wider than the parent.

No references cited.

ROBERT E. BAGWILL, Primary Examiner